(12) United States Patent
Martinez et al.

(10) Patent No.: US 10,253,308 B2
(45) Date of Patent: Apr. 9, 2019

(54) REACTION MIXTURES

(71) Applicant: Roche Molecular Systems, Inc., Pleasanton, CA (US)

(72) Inventors: Tomas R. Martinez, Concord, CA (US); Edward S. Smith, San Francisco, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/818,034

(22) Filed: Nov. 20, 2017

(65) Prior Publication Data

US 2018/0073008 A1 Mar. 15, 2018

Related U.S. Application Data

(63) Continuation of application No. 14/958,645, filed on Dec. 3, 2015, now Pat. No. 9,868,944.

(60) Provisional application No. 62/094,284, filed on Dec. 19, 2014.

(51) Int. Cl.
*C12N 9/96* (2006.01)
*C12N 9/12* (2006.01)

(52) U.S. Cl.
CPC ............ *C12N 9/96* (2013.01); *C12N 9/1252* (2013.01); *C12Y 207/07007* (2013.01)

(58) Field of Classification Search
CPC ................................ C12N 9/96; C12N 9/1252
See application file for complete search history.

(56) References Cited

U.S. PATENT DOCUMENTS

| | | |
|---|---|---|
| 5,861,251 A | 1/1999 | Park et al. |
| 6,153,412 A | 11/2000 | Park et al. |
| 7,179,890 B2 | 2/2007 | Smith et al. |
| 7,407,747 B2 | 8/2008 | Perry et al. |
| 2003/0119042 A1 | 6/2003 | De Sarabia Rosado et al. |

FOREIGN PATENT DOCUMENTS

| | | |
|---|---|---|
| WO | 0014505 A1 | 3/2000 |
| WO | 2005103277 A1 | 11/2005 |
| WO | 2008036544 A1 | 3/2008 |

OTHER PUBLICATIONS

Ivanova et al., 2013; Protocols for dry DNA storage and shipment at room temperature. Molecular Ecology Resources 13:890-898.*
Wang, W., "Lyophilization and development of solid protein pharmaceuticals." International Journal of Pharmacuetics 200: 1-60, 2000.
Kasper, J.C. et al., "The freezing step in lyophilization: Physicochemical fundamentals, freezing methods and consequences on process performance and quality attributes of biopharmaceuticals." European Journal of Pharmaceutics and Biopharmaceutics 78:248-263, 2011.
Franks, F., "Freeze-drying of bioproducts: putting principles into practice." European Journal of Pharmaceutics and Biopharmaceutics 45:221-229, 1998.
Colaco C. et al., "Extraordinary stability of enzymes dried in trehalose: Simplified molecular biology", Nature Biotechnology, 10 (9): 1007-1011, 1992.
Handique, A.K., "New technique for thermostability of restriction and modifying enzymes", Current Science, 66 (2): 103-104, 1994.

* cited by examiner

*Primary Examiner* — Karen Cochrane Carlson
(74) *Attorney, Agent, or Firm* — David J. Chang

(57) ABSTRACT

The present invention provides stable dried reaction mixtures, methods for their preparation, methods for their use, and kits comprising them. The stable dried reaction mixtures are useful in many recombinant DNA techniques, especially nucleic acid amplification by the polymerase chain reaction (PCR).

6 Claims, 11 Drawing Sheets

A

B

A

B

A

B

A

B

REACTION MIXTURES

CROSS-REFERENCE TO RELATED INVENTION

This application is a continuation of U.S. patent application Ser. No. 14/958,645, filed Dec. 3, 2015, which claims the benefit of priority of U.S. Provisional Patent Application Ser. No. 62/094,284, filed Dec. 19, 2014, both of which are incorporated herein by reference in their entireties.

FIELD OF THE INVENTION

The present invention provides stable reaction mixtures, methods for their preparation, methods for their use, and kits comprising them. The stable reaction mixtures are useful in many recombinant DNA techniques, especially nucleic acid amplification by the polymerase chain reaction (PCR).

BACKGROUND OF THE INVENTION

To address the challenge of producting stable polypeptide compositions, proteins are typically prepared in solid form to provide an acceptable shelf life. A standard method for preparing solid form protein compositions is lyophilization (freeze-drying) but this process creates stresses which can denature proteins to varying degrees (Wang, W. (2000) International Journal of Pharmaceutics 203; 1-60). Few biological reaction compounds are stable in solubilized form for any length of time and this is especially true for storage at room temperature. Consequently, numerous studies have been performed to evaluate possibilities to enhance the storage capabilities of biological reaction compounds in dry form. It is generally accepted that it will be necessary to use at least one stabilizing additive in order to assure the biological activity of e.g. a polymerase upon re-solubilization.

WO 2008/36544 describes the use of so-called filler materials in order to provide dried compositions, the filler materials are e.g. carbohydrates such as FICOLL, sucrose, glucose, trehalose, melezitose, DEXTRAN or mannitol, proteins such BSA, gelatin or collagen and polymers such as PEG or polyvinyl pyrrolidone (PVP). Glass-forming filler materials for stabilizing biological reagents are further described in U.S. Pat. Nos. 5,098,893, 5,200,399 and 5,240,843. The filler material FICOLL is a copolymer disclosed in U.S. Pat. No. 3,300,474. The methods of drying the liquid reaction mixtures are most of the time very complex in nature and therefore, the drying procedures are demanding and expensive.

Freeze-drying (U.S. Pat. No. 5,593,824) or vacuum drying (U.S. Pat. No. 5,565,318) is used for drying the biological materials in a carbohydrate polymer matrix. Lyophilization or freeze-drying is a well established technique towards storage of proteins that is disclosed in many state of the art documents (e.g. Passot, S., et al., Pharmaceutical Development and Technology 12 (2007) 543-553; Carpenter, J. F., et al., Pharmaceutical Research 14 (8) (1997) 969-975; Schwegman, J. J., et al., Pharmaceutical Development and Technology 10 (2005) 151-173).

A selection of drying conditions for different reaction mixtures for sequencing applications comprising genetic modifications of the Taq polymerase are described in U.S. Pat. No. 7,407,747. Drying procedures used are freeze-drying, speedvac without additional heat, speedvac with additional heat and air drying at room temperature. The reaction mixtures within this patent were tested with respect to a variety of cryoprotectants such as trehalose, sucrose, glucose and trimethylamine-N-oxide (TMANO). Moreover, experiments were also performed without cryoprotectants at all, but no data was disclosed concerning the stability of those reaction mixtures with time. A good stability for as long as 8 weeks was reported only for reaction mixtures comprising trehalose and bovine serum albumin (BSA).

Moreover, U.S. Pat. No. 7,407,747 discloses experiments with the polymerase in different sequencing mixtures where each sequencing mixture comprises different compositions of buffer solution, nucleotide triphosphates, and nucleotides with fluorescence label and primers. However, there is no disclosure if a polymerase in mixtures for real-time PCR amplifications, namely mixtures comprising buffer solution, nucleotides triphosphates, primers and detection probes, may be dried and stored without affecting the PCR activity of the polymerase.

U.S. Pat. No. 8,652,811 discloses a method to dry a Taq DNA polymerase within a real-time PCR mixture, whereas the obtained dry composition can be stored without affecting the PCR performance of the Taq DNA polymerase.

BRIEF SUMMARY OF THE INVENTION

The present invention provides for stable reaction mixtures used for nucleic acid amplification by PCR and RT-PCR (Reverse Transcriptase-PCR) that comprises a saccharide (for example, sucrose) which have been dried down without the need for lyophilization or freeze-drying. The present invention also provides for methods for preparing dried-down reaction mixtures.

Therefore in one aspect, the present invention involves a dry reaction mixture composition comprising at least one nucleic acid amplification-related enzyme, nucleoside monomers, and a saccharide, wherein the composition is non-lyophilized. In another aspect, the present invention involves a method of preparing a dry reaction mixture composition, the method comprising drying a reaction mixture in aqueous form in the absence of lyophilization, wherein the reaction mixture in aqueous form comprises at least one nucleic acid amplification-related enzyme, nucleoside monomers, and a saccharide. The embodiments and advantages of the invention are described in more detail in the Detailed Description of the Invention and in the Figures.

DETAILED DESCRIPTION OF THE INVENTION

Figure 1:
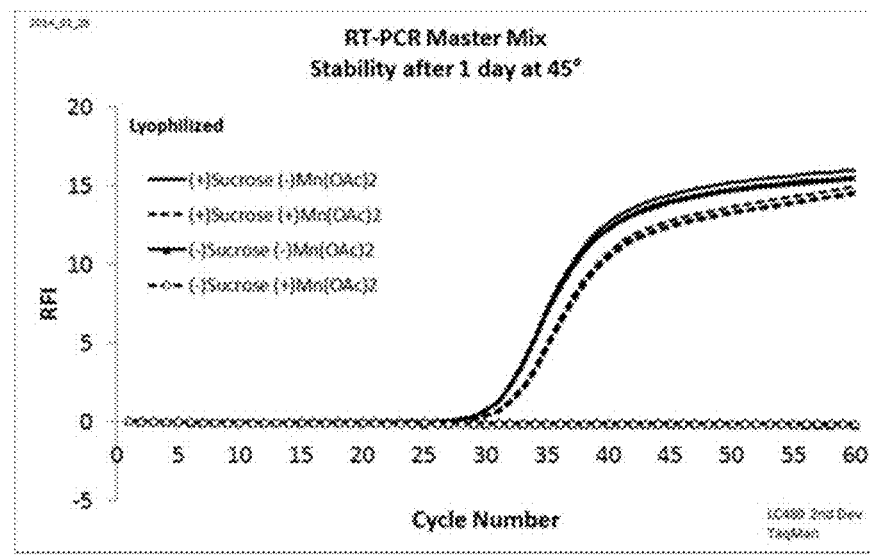
FIG. 1 shows the RT-PCR growth curves generated by the lyophilized (A) and non-lyophilized (B) dry reaction mastermixes on day 1 of storage at 42° C.
Figure 1:
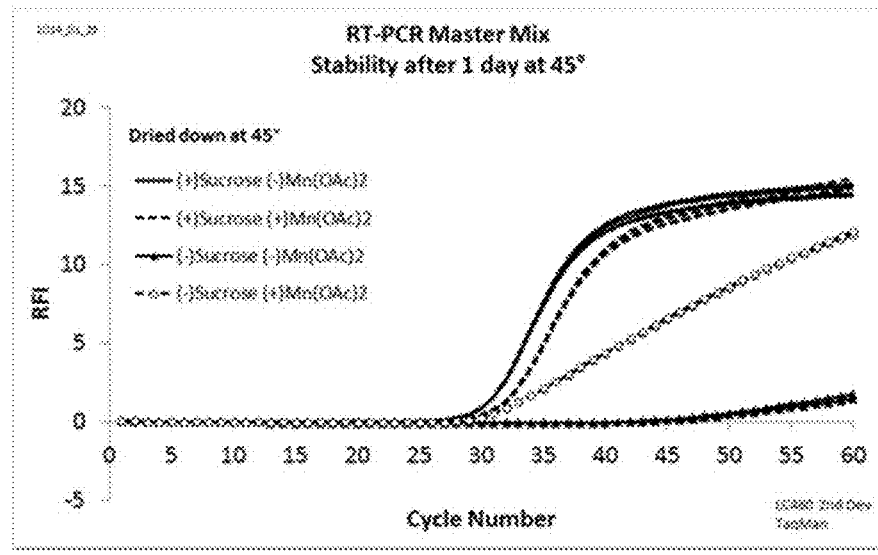
Figure 2:
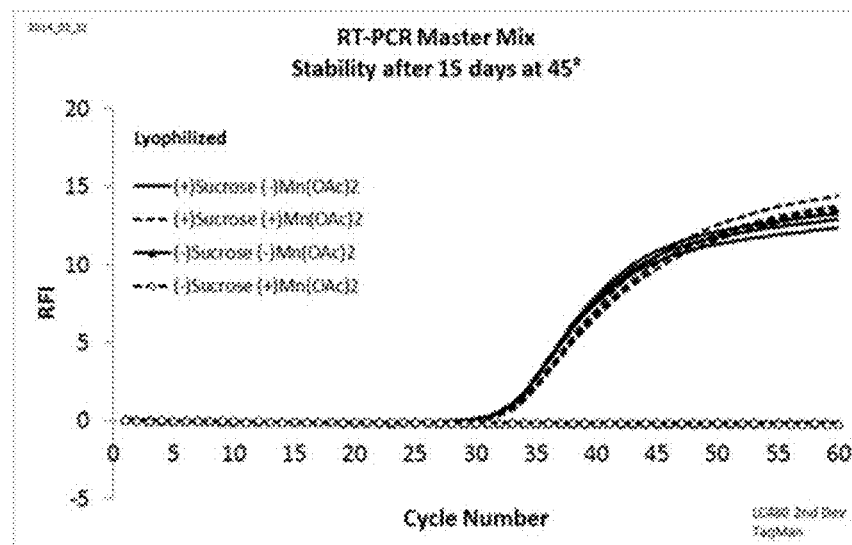
FIG. 2 shows the RT-PCR growth curves generated by the lyophilized (A) and non-lyophilized (B) dry reaction mastermixes on day 15 of storage at 42° C.
Figure 2:
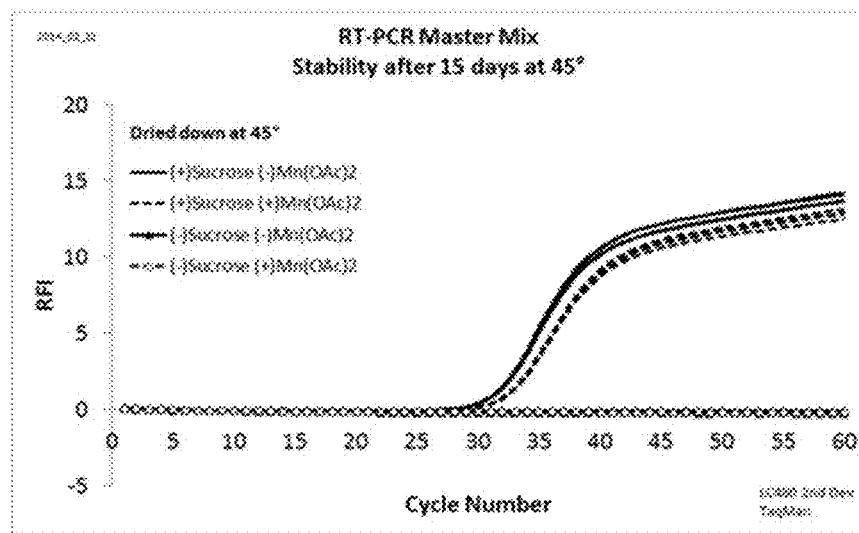
Figure 3:
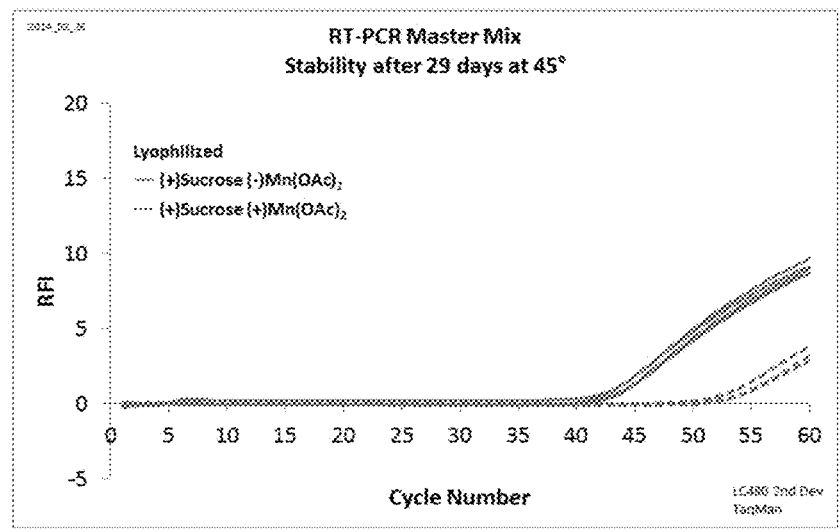
FIG. 3 shows the RT-PCR growth curves generated by the lyophilized (A) and non-lyophilized (B) dry reaction mastermixes on day 29 of storage at 42° C.
Figure 3:
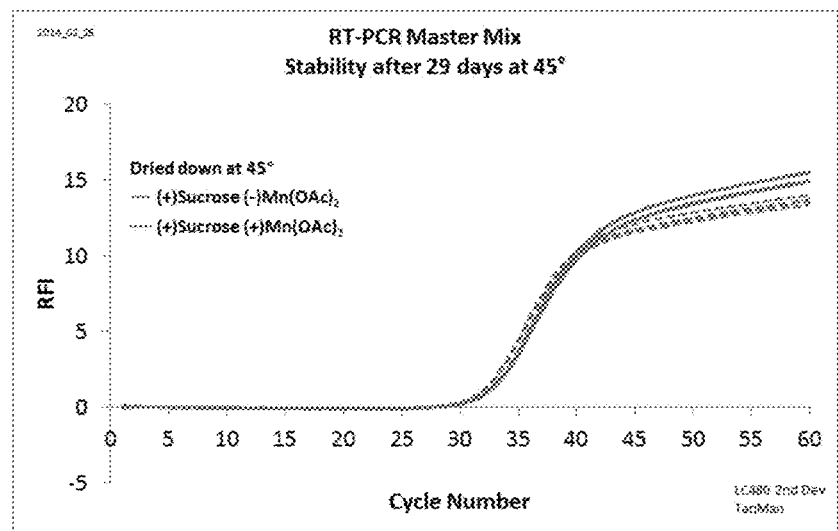
Figure 4:
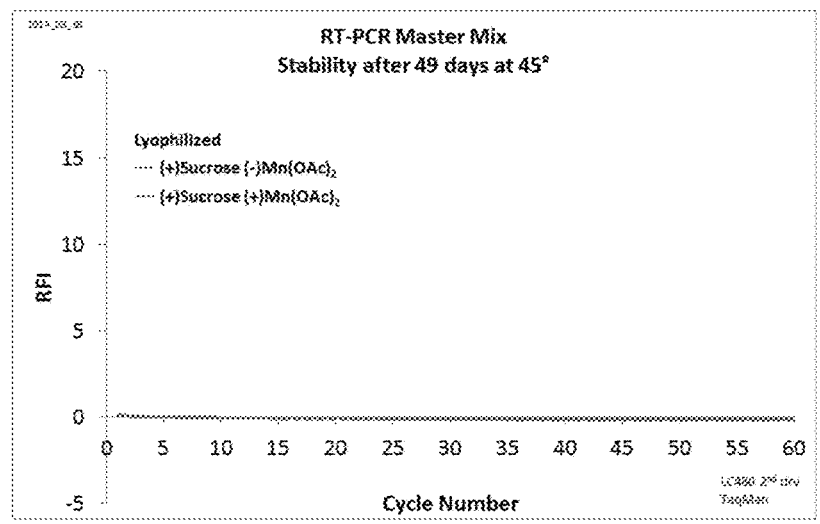
FIG. 4 shows the RT-PCR growth curves generated by the lyophilized (A) and non-lyophilized (B) dry reaction mastermixes on day 49 of storage at 42° C.
Figure 4:
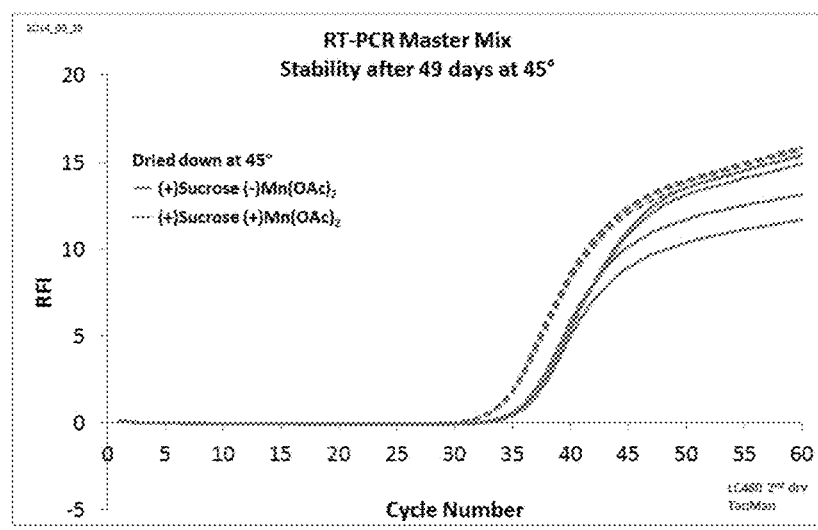

The present invention provides stable reaction mixtures, methods for their preparation, methods for their use, and kits comprising them. The stable reaction mixtures are useful in many recombinant DNA techniques, especially nucleic acid amplification by the polymerase chain reaction (PCR). In particular, the present invention provides stable non-lyophilized reaction mixtures containing an enzyme (e.g., an enzyme used in nucleic acid amplification) and a sugar. Such enzyme mixtures may be dried down in the absence of lyophilization and stored long term at room temperature without significant loss of enzyme activity.

I. Definitions

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The term "lyophilization" refers to the creation of a stable preparation of a biological substance by rapid freezing and dehydration of the frozen product under high vacuum and is also commonly referred as "freeze-drying".

The term "non-lyophilized", "dried down" or "dried" refers to a process for drying down a biological substance by not utilizing the process of lyophilization.

The term "ambient temperature" refers to the temperature of the surrounding and is synonymous with "room temperature" when referring to the temperature of a temperature-controlled indoor building. Typically, ambient temperature refers to a temperature range of between 15° C. and 25° C. although slightly cooler or warmer temperatures may still be considered within the range of ambient temperature.

The term "aptamer" refers to a single-stranded DNA that recognizes and binds to DNA polymerase, and efficiently inhibits the polymerase activity as described in U.S. Pat. No. 5,693,502, hereby expressly incorporated by reference herein in its entirety. Use of aptamer and dUTP/UNG in RT-PCR is also discussed, for example, in Smith, E. S. et al, (Amplification of RNA: High-temperature Reverse Transcription and DNA Amplification with a Magnesium-activated Thermostable DNA Polymerase, in PCR Primer: A Laboratory Manual, 2nd Edition, Dieffenbach, C. W. and Dveksler, G. S., Ed., Cold Spring Harbor Laboratory Press, Cold Spring Harbor, N.Y., 211-219, (2003)).

"Recombinant", as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by restriction endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

The term "oligonucleotide" refers to a nucleic acid that includes at least two nucleic acid monomer units (e.g., nucleotides). An oligonucleotide typically includes from about six to about 175 nucleic acid monomer units, more typically from about eight to about 100 nucleic acid monomer units, and still more typically from about 10 to about 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. (*J. Am. Chem. Soc.* 103:3185-3191, 1981); automated synthesis methods; or the solid support method of Caruthers et al. U.S. Pat. No. 4,458,066, or other methods known to those skilled in the art. All of these references are incorporated by reference.

The term "primer" as used herein refers to a polynucleotide capable of acting as a point of initiation of template-directed nucleic acid synthesis when placed under conditions in which polynucleotide extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction)). To further illustrate, primers can also be used in a variety of other oligonuceotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 40 nucleotides, more typically from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur. In certain embodiments, the term "primer pair" means a set of primers including a 5' sense primer (sometimes called "forward") that hybridizes with the complement of the 5' end of the nucleic acid sequence to be amplified and a 3' antisense primer (sometimes called "reverse") that hybridizes with the 3' end of the sequence to be amplified (e.g., if the target sequence is expressed as RNA or is an RNA). A primer can be labeled, if desired, by incorporating a label detectable by spectroscopic, photochemical, biochemical, immunochemical, or chemical means. For example, useful labels include $^{32}$P, fluorescent dyes, electron-dense reagents, enzymes (as commonly used in ELISA assays), biotin, or haptens and proteins for which antisera or monoclonal antibodies are available.

The term "conventional" or "natural" when referring to nucleic acid bases, nucleoside triphosphates, or nucleotides refers to those which occur naturally in the polynucleotide being described (i.e., for DNA these are dATP, dGTP, dCTP and dTTP). Additionally, dITP, and 7-deaza-dGTP are frequently utilized in place of dGTP and 7-deaza-dATP can be utilized in place of dATP in in vitro DNA synthesis reactions, such as sequencing. Collectively, these may be referred to as dNTPs.

The term "unconventional" or "modified" when referring to a nucleic acid base, nucleoside, or nucleotide includes modification, derivations, or analogues of conventional bases, nucleosides, or nucleotides that naturally occur in a particular polynucleotide. Certain unconventional nucleotides are modified at the 2' position of the ribose sugar in comparison to conventional dNTPs. Thus, although for RNA the naturally occurring nucleotides are ribonucleotides (i.e., ATP, GTP, CTP, UTP, collectively rNTPs), because these nucleotides have a hydroxyl group at the 2' position of the sugar, which, by comparison is absent in dNTPs, as used herein, ribonucleotides are unconventional nucleotides as substrates for DNA polymerases. As used herein, unconventional nucleotides include, but are not limited to, compounds used as terminators for nucleic acid sequencing. Exemplary terminator compounds include but are not limited to those compounds that have a 2',3' dideoxy structure and are referred to as dideoxynucleoside triphosphates. The dideoxynucleoside triphosphates ddATP, ddTTP, ddCTP and ddGTP are referred to collectively as ddNTPs. Additional examples of terminator compounds include 2'-PO$_4$ analogs of ribonucleotides (see, e.g., U.S. Application Publication Nos. 2005/0037991 and 2005/0037398, which are both incorporated by reference). Other unconventional nucleotides include phosphorothioate dNTPs ([α-S]dNTPs), 5'-[α-borano]-dNTPs, [α]-methyl-phosphonate dNTPs, and ribonucleoside triphosphates (rNTPs). Unconventional bases may be labeled with radioactive isotopes such as $^{32}$P, $^{33}$P, or $^{35}$S; fluorescent labels; chemiluminescent labels; bioluminescent labels; hapten labels such as biotin; or enzyme labels such as streptavidin or avidin. Fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include Texas Red, ROX, R110, R6G, and TAMRA. Various dyes or nucleotides labeled with FAM, HEX, TET, JOE, NAN, ZOE, ROX, R110, R6G, Texas Red and TAMRA are marketed by Perkin-Elmer (Boston, Mass.), Applied Biosystems (Foster City, Calif.), or Invitrogen/Molecular Probes (Eugene, Oreg.). Dyes of the cyanine family include Cy2, Cy3, Cy5, and Cy7 and are marketed by GE Healthcare UK Limited (Amersham Place, Little Chalfont, Buckinghamshire, England).

The term "Cp value" or "crossing point" value refers to a value that allows quantification of input target nucleic acids. The Cp value can be determined according to the second-derivative maximum method (Van Luu-The, et al., "Improved real-time RT-PCR method for high-throughput measurements using second derivative calculation and double correction," BioTechniques, Vol. 38, No. 2, February 2005, pp. 287-293). In the second derivative method, a Cp corresponds to the first peak of a second derivative curve. This peak corresponds to the beginning of a log-linear phase. The second derivative method calculates a second derivative value of the real-time fluorescence intensity curve, and only one value is obtained. The original Cp method is based on a locally defined, differentiable approximation of the intensity values, e.g., by a polynomial function. Then the third derivative is computed. The Cp value is the smallest root of the third derivative. The Cp can also be determined using the fit point method, in which the Cp is determined by the intersection of a parallel to the threshold line in the log-linear region (Van Luu-The, et al., BioTechniques, Vol. 38, No. 2, February 2005, pp. 287-293). The Cp value provided by the LightCycler instrument offered by Roche by calculation according to the second-derivative maximum method.

The term "PCR efficiency" refers to an indication of cycle to cycle amplification efficiency. PCR efficiency is calculated for each condition using the equation: % PCR efficiency=$(10^{(-slope)}-1) \times 100$, wherein the slope was calculated by linear regression with the log copy number plotted on the y-axis and Cp plotted on the x-axis. PCR efficiency can be measured using a perfectly matched or mismatched primer template.

The term "FRET" or "fluorescent resonance energy transfer" or "Foerster resonance energy transfer" refers to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™ (Integrated DNA Tech., Inc., Coralville, Iowa), and BlackBerry™ Quencher 650 (BBQ-650) (Berry & Assoc., Dexter, Mich.).

The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants. The cells can be prokaryotic or eukaryotic.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, positive retroregulatory elements (see U.S. Pat. No. 4,666,848, incorporated herein by reference), and possibly other sequences. Eucaryotic cells are known to utilize promoters, polyadenylation signals, and enhancers.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The terms "restriction endonucleases" and "restriction enzymes" refer to enzymes, typically bacterial in origin, which cut double-stranded DNA at or near a specific nucleotide sequence.

Families of amino acid residues having similar side chains are defined herein. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), beta-branched side chains (e.g., threonine, valine, isoleucine) and aromatic side chains (e.g., tyrosine, phenylalanine, tryptophan, histidine).

The term "reagent solution" is any solution containing at least one reagent needed or used for PCR purposes. Most typical ingredients are polymerase, nucleotide, primer, ions, magnesium, salts, pH buffering agents, nucleotide triphosphates (NTPs) or deoxynucleotide triphosphates (dNTPs), probe, fluorescent dye (may be attached to probe), nucleic acid binding agent, a nucleic acid template. The reagent may also be other polymerase reaction additive, which has an influence on the polymerase reaction or its monitoring.

The term "mastermix" refers to a mixture of all or most of the ingredients or factors necessary for PCR to occur, and in some cases, all except for the template and primers which are sample and amplicon specific. Commercially available mastermixes are usually concentrated solutions. A mastermix may contain all the reagents common to multiple samples, but it may also be constructed for one sample only. Using mastermixes helps to reduce pipetting errors and variations between samples due to differences between pipetted volumes.

The term "thermostable polymerase" refers to an enzyme that is stable to heat, is heat resistant and retains sufficient activity to effect subsequent primer extension reactions after being subjected to the elevated temperatures for the time necessary to denature double-stranded nucleic acids. Heating conditions necessary for nucleic acid denaturation are well known in the art and are exemplified in U.S. Pat. Nos. 4,965,188 and 4,889,818, which are incorporated herein by reference. As used herein, a thermostable polymerase is suitable for use in a temperature cycling reaction such as PCR. The examples of thermostable nucleic acid polymerases include *Thermus aquaticus* Taq DNA polymerase, Thermus sp. Z05 polymerase, *Thermus flavus* polymerase, *Thermotoga maritima* polymerases, such as TMA-25 and TMA-30 polymerases, Tth DNA polymerase, and the like.

A "modified" thermostable polymerase refers to a polymerase in which at least one monomer differs from the reference sequence, such as a native or wild-type form of the polymerase or another modified form of the polymerase. Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. The examples of modified thermostable polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "thermoactive polymerase" refers to an enzyme that is active at the elevated temperatures necessary to ensure specific priming and primer extension (e.g., 55-80° C.).

The terms "peptide," "polypeptide," and "protein" are used interchangeably. The terms "nucleic acid" and "polynucleotide" are used interchangeably. Amino acid sequences are written from amino terminus to carboxy terminus, unless otherwise indicated. Single-stranded nucleic acid sequences are written 5' to 3', unless otherwise indicated. The top strand of a double-stranded nucleic acid sequence is written 5' to 3', and the bottom strand is written 3' to 5', unless otherwise indicated.

II. Dry Reaction Mixture Compositions

The dry reaction mixture composition of the present invention comprises of at least one nucleic acid amplification-related enzyme, nucleotide triphosphates, and a saccharide, wherein the composition is non-lyophilized. The dry reaction mixture of the present invention has improved stability compared to a dry reaction mixture that lacks a saccharide or that is lyophilized, or that both lacks a saccharide and is lyophilized. In one embodiment of the dry reaction mixture, the saccharide is chosen from sucrose, trehalose, dextrose, lactose, maltose, trehalose, cyclodextrins, maltodextrins and dextrans. In another embodiment, the dry reaction mixture retains activity upon storage under conditions that are, or are equivalent to, 45° C. for 3 months. In another embodiment, the dry reaction mixture retains activity upon storage under conditions that are, or are equivalent to ambient temperature for 12 months. In yet another embodiment, the dry reaction mixture has at least one component selected from the group consisting of an aptamer, a detergent, a buffer, a salt and an oligonucleotide. In yet another embodiment, the dry reaction mixture further comprises manganese acetate ($Mn(OAc)_2$). In still another embodiment, the dry reaction mixture has an amplification-related enzyme that is a thermostable polymerase that is selected from the group consisting of *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, as well as modified thermostable polymerases, or any combination thereof. In still another embodiment, the dry reaction mixture composition has an saccharide that is present in an amount such that if the composition is reconstituted in aqueous solution, the concentration of the saccharide is between about 50 mM to about 1000 mM. In one further embodiment, the saccharide is sucrose.

III. Method of Preparing Dry Reaction Mixture Compositions

The dry reaction mixture composition of the present invention is prepared by drying the reaction mixture in aqueous form in the absence of lyophilization, wherein the reaction mixture in aqueous form comprises at least one nucleic acid amplification-related enzyme, nucleotide triphosphates, and a saccharide. In one embodiment, the drying is performed at ambient temperature. In another embodiment, the saccharide in the dry reaction mixture is at a concentration between about 50 mM and about 1000 mM in the reaction mixture in aqueous form. In one further embodiment, the saccharide is sucrose. In yet another embodiment, the dry reaction mixture further comprises manganese acetate ($Mn(OAc)_2$). In still another embodiment, the dry reaction mixture has an amplification-related enzyme that is a thermostable polymerase that is selected from the group consisting of *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, as well as modified thermostable polymerases, or any combination thereof. In yet another embodiment, the dry reaction mixture composition prepared using the method of the present invention retains activity upon storage under conditions that are, or are equivalent to, 45° C. for 3 months. In yet another embodiment, the dry reaction mixture composition prepared using the method of the present invention retains activity upon storage under conditions that are, or are equivalent to, ambient temperature for 12 months.

While the foregoing invention has been described in some detail for purposes of clarity and understanding, it will be clear to one skilled in the art from a reading of this disclosure that various changes in form and detail can be made without departing from the true scope of the invention. For example, all the compositions and methods described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The following examples are given to illustrate embodiments of the present invention as it is presently preferred to practice. It will be understood that the examples are illustrative, and that the invention is not be considered as restricted except as indicated in the appended claims.

EXAMPLES

Example 1: Preparation of Dry Reaction 5×RT-PCR Mastermixes

Dry Reaction 5×RT-PCR mastermixes were first prepared from aqueous solutions with the following composition: 250 mM Tricine (pH 8.3), 500 mM KOAc (pH 7.5), 0.05% Tween 20, 1.326 µM Aptamer (used for hot-start PCR), 1000 µm dATP, 1000 µm dCTP, 1000 µm dGTP, 1500 µm dUTP, 150 µm dTTP, 0.029% NaN$_3$, 0.5 mM EDTA, 0.2 U/µl uracil-N-glycosylase (UNG), 2.2 U/µl Z05-D DNA polymerase. 1.5M sucrose was added in half of the 5×RT-PCR mastermixes [(+) sucrose] and not added in the other half of the 5×RT-PCR mastermixes [(−) sucrose]. One set of (+) sucrose and (−) sucrose 5×RT-PCR mastermixes were dried down by lyophilization and incubated at 45° C. The other set of (+) sucrose and (−) sucrose 5×RT-PCR mastermixes were dried down at 45° C. in uncapped tubes and incubated at 45° C. Stability of the Dry Reaction 5×RT-PCR mastermixes was determined by performing RT-PCR over a 3 month period.

Example 2: Analysis of the Dry Reaction Mastermixes by RT-PCR

The Dry Reaction RT-PCR Mastermixes were reconstituted to 1× concentration and analyzed in RT-PCR reaction. Reverse transcription and amplification of the RNA target was performed according to the protocol of the GeneAmp® Gold RNA PCR Reagent Kit (P/N 4308206, Applied Biosystems, Foster City, Calif.). Briefly, 1×10$^4$ input copies of control pAW109 RNA transcript was added to 0.2 µM each of DM151 and DM152 primers which yields a 308 base pair target from the IL-1α gene. The amplified product was detected using the TaqMan probe AL42F at 0.1 µM concentration. In some reactions, manganese acetate (Mn(OAc)$_2$) was added to a final concentration of 1.5 mM. RT-PCR was performed on a LightCycler® 480 Instrument (Roche Diagnostics) with the reverse transcription phase conducted at 55° C. for 5 minutes, 60° C. for 5 minutes and 65° C. for 5 minutes, followed by PCR at 92° C. for 15 seconds and 60° C. for 40 seconds with 55 cycles.

Example 3: Results of RT-PCR Reactions

Figure 5:
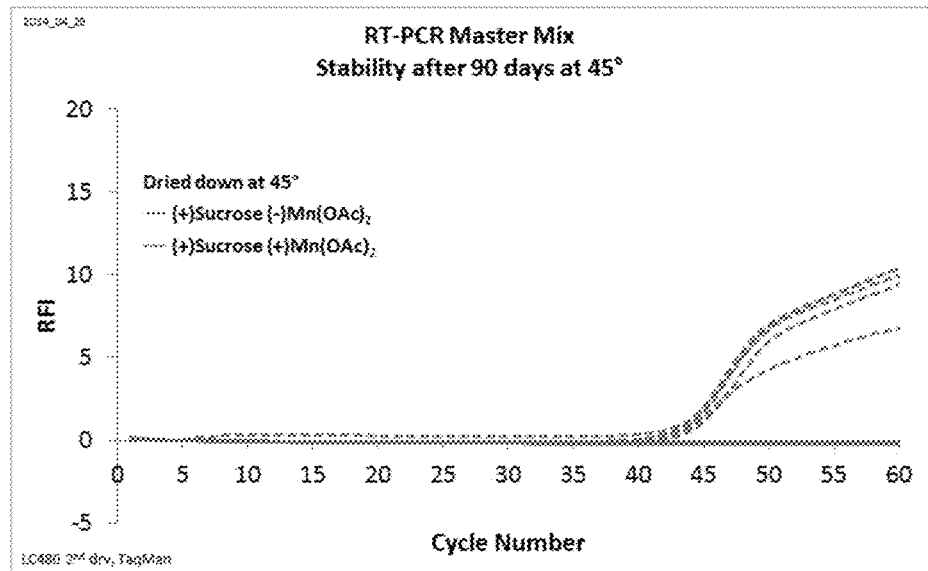
FIG. 5 shows the RT-PCR growth curves generated by the non-lyophilized dry reaction mastermixes on day 90 of storage at 42° C.

RT-PCR reactions were performed on the Dry Reaction RT-PCR Mastermixes which had been stored for 1 day, 15 days, 29 days, 49 days, and 90 days and the results of the RT-PCR reactions conducted on each of the days are depicted in the growth curves shown in FIGS. 1-5. After 1 day, both the lyophilized and the dried down (+) sucrose mastermixes were stable while the lyophilized (−) sucrose mastermix was completely degraded and the dried down (−) sucrose mastermix started to show degradation (FIG. 1A, B). After 15 days, both the lyophilized and dried down (+) sucrose mastermixes were stable and showed similar growth curves (FIG. 2A,B). After 29 days, the lyophilized (+) mastermixes started showing degradation with more degradation observed in mastermixes not containing manganous acetate (FIG. 3A). In contrast, the dried down (+) mastermixes were still stable with growth curves that showed little difference from the growth curves on day 15 (FIG. 3B). After 49 days, the lyophilized (+) sucrose mastermixes were completely degraded (FIG. 4A) whereas the dried down (+) sucrose mastermixes containing Mn(OAc)$_2$ was still stable. Finally, after 90 days, the dried down (+) sucrose mastermixes with no Mn(OAc)2 was completely degraded and the mastermixes with Mn(OAc)2 showed some degradation but were still able to generate growth curves (FIG. 5). These results clearly show not only the stabilizing effects of sucrose and manganese acetate but also the superior performance of a non-lyophilized mastermix when compared with a lyophilized mastermix.

Example 4: Preparation and Analysis of Dry Reaction 5×RT-PCR Mastermixes at Ambient Temperature Dry Reaction 5×RT-PCR mastermixes with the composition as described in Example 1 (with or without sucrose in the master mix) were pipetted into 2 ml polypropylene tubes. Mn(OAc)$_2$ was added to half of the tubes and the other half were left without Mn(OAc)$_2$. These samples where dried down at 45° C. and at atmospheric pressure in the uncapped 2 ml polypropylene tubes. At the end of 7 days at 45° C., the 2 ml tubes were capped and stored at ambient room temperature protected from light. Stability time points were determined over a one year period. These mastermixes were analyzed by RT-PCR reactions using the amplification reagents and conditions as described in Example 2.

Figure 6:
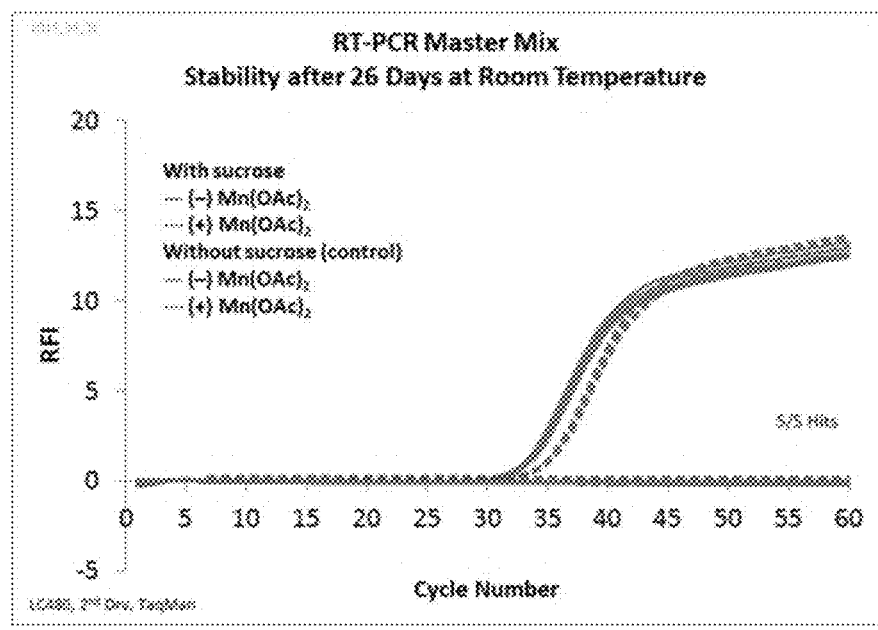
FIG. 6 shows the RT-PCR growth curves generated by the non-lyophilized dry reaction mastermixes on day 26 of storage at ambient temperature.
Figure 7:
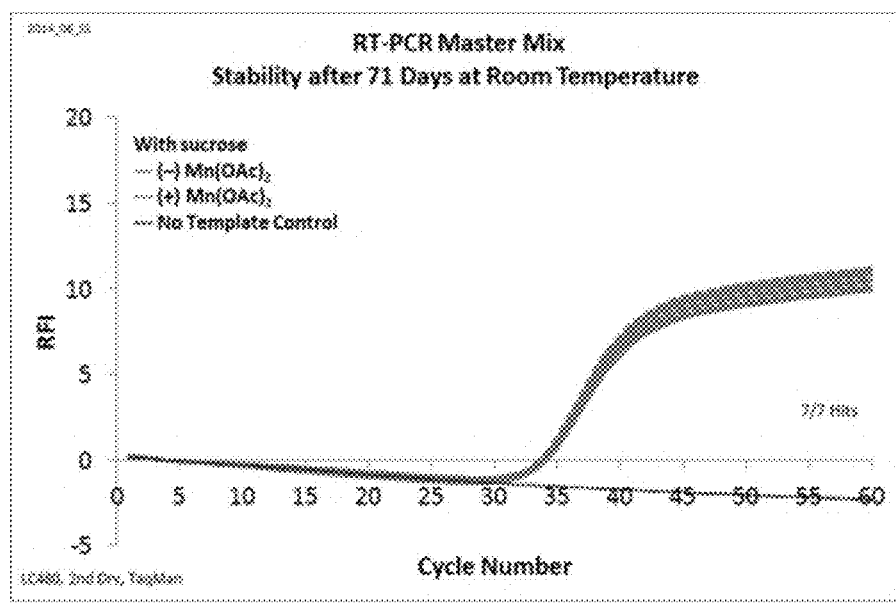
FIG. 7 shows the RT-PCR growth curves generated by the non-lyophilized dry reaction mastermixes on day 71 of storage at ambient temperature.
Figure 8:
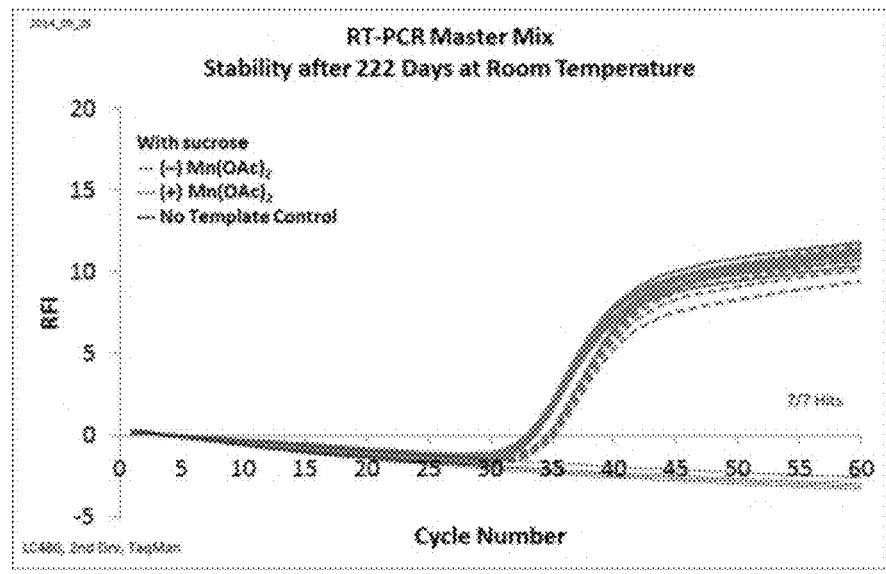
FIG. 8 shows the RT-PCR growth curves generated by the non-lyophilized dry reaction mastermixes on day 222 of storage at ambient temperature.
Figure 9:
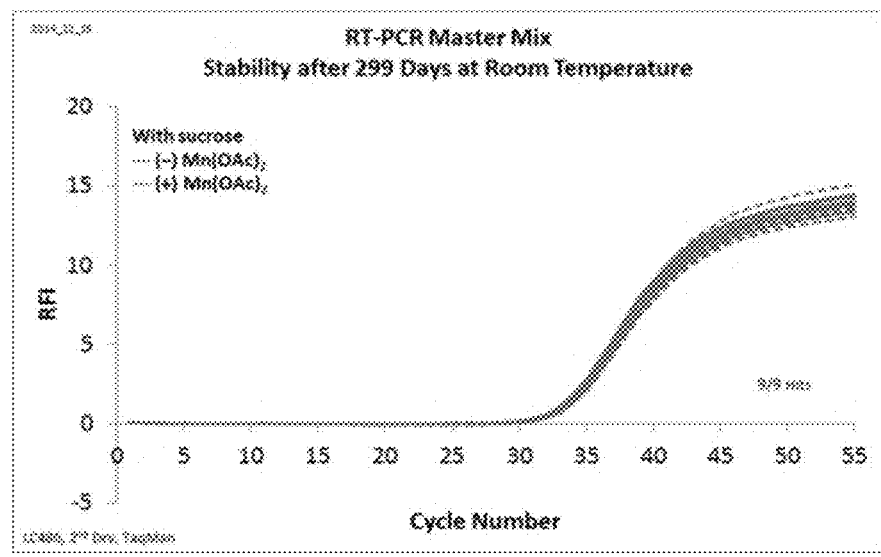
FIG. 9 shows the RT-PCR growth curves generated by the non-lyophilized dry reaction mastermixes on day 299 of storage at ambient temperature.
Figure 10:
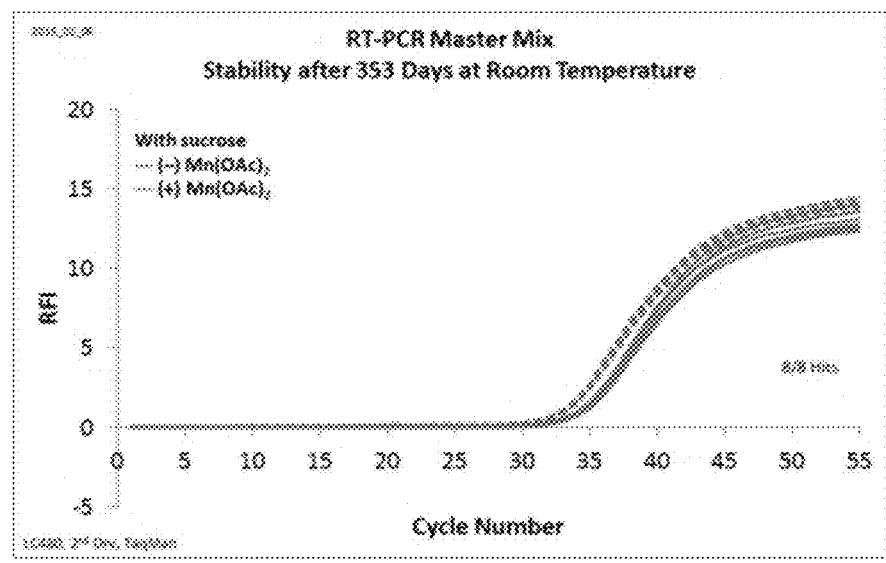
FIG. 10 shows the RT-PCR growth curves generated by the non-lyophilized dry reaction mastermixes on day 353 of storage at ambient temperature.
Figure 11:
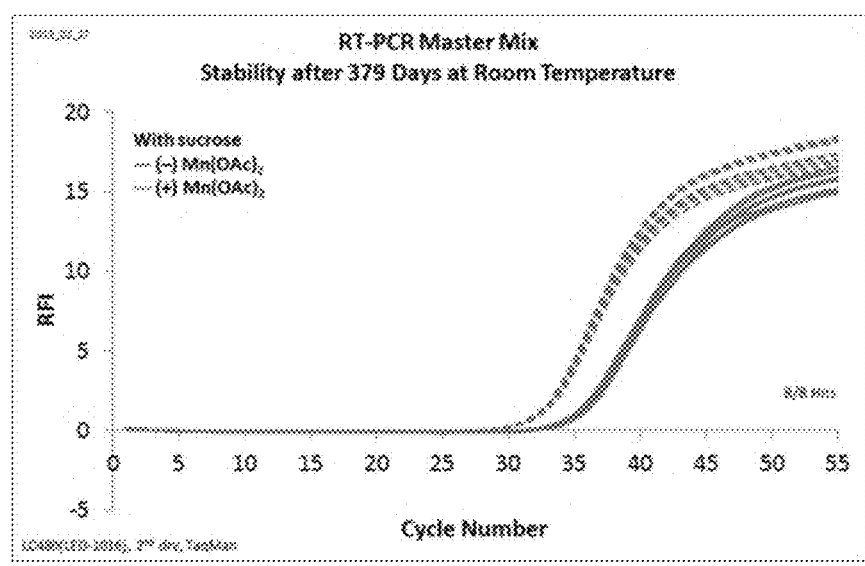
FIG. 11 shows the RT-PCR growth curves generated by the non-lyophilized dry reaction mastermixes on day 379 of storage at ambient temperature.

The results of the RT-PCR reactions are depicted in the growth curves shown in FIGS. 6-11. FIG. 6 shows that after 26 days at ambient (room) temperature, the dried down RT-PCR mastermixes with sucrose were stable and generated curve growths whereas the dried down RT-PCR mastermixes without sucrose were completed degraded and generated no growth curves. The RT-PCR mastermixes with sucrose showed stability in storage at ambient temperature after 71 days (FIG. 7), 222 days (FIG. 8), 299 days (FIG. 9), 353 days (FIG. 10) and 379 days (FIG. 11). RT-PCR mastermix that was dried down with added Mn(OAc)$_2$ showed equal or greater stability than the same material dried down without the metal. These RT-PCR results showed that efficient amplification was achieved with the RT-PCR Master Mix formulations with sucrose after more than 12 months of sitting in the dark at ambient (room) temperature.

What is claimed is:

1. A dry reaction mixture composition comprising at least one nucleic acid amplification-related enzyme, nucleotide triphosphates, manganese acetate (Mn(OAc)2), and sucrose, wherein the composition is air-dried at 45° C. and is non-lyophilized, and wherein the composition has improved stability compared to a reaction mixture which is (i) lyophilized; and (ii) lacking sucrose.

2. The composition of claim 1, wherein the dry reaction mixture retains activity upon storage under conditions that are, or are equivalent to, 45° C. for 3 months.

3. The composition of claim 1, further comprising at least one component selected from the group consisting of an aptamer, a detergent, a buffer, a salt, and an oligonucleotide.

4. The composition of claim 1, wherein said at least one nucleic acid amplification-related enzyme is a thermostable polymerase selected from the group consisting of *Thermus aquaticus* Taq DNA polymerase, *Thermus* sp. Z05 polymerase, *Thermus* sp. Z05-D polymerase, *Thermus flavus* polymerase, *Thermotoga maritima* polymerase, TMA-25 polymerase, TMA-30 polymerase, Tth DNA polymerase, as well as modified thermostable polymerases, or any combination thereof.

5. The composition of claim 4 wherein said at least one nucleic acid amplification-related enzyme is a thermostable polymerase selected from *Thermus* sp. Z05 polymerase or *Thermus* sp. Z05-D polymerase.

6. The composition of claim 1, wherein sucrose is present in an amount such that if the composition is reconstituted in aqueous solution, the concentration of sucrose is between about 50 mM to about 1000 mM.

* * * * *